United States Patent [19]

Vuorinen

[11] Patent Number: 5,563,303
[45] Date of Patent: Oct. 8, 1996

[54] PRODUCTION OF XYLITOL

[75] Inventor: Tapani Vuorinen, Espoo, Finland

[73] Assignee: Amylum, n.v., Brussels, Belgium

[21] Appl. No.: 295,791

[22] PCT Filed: Mar. 17, 1993

[86] PCT No.: PCT/BE93/00013

§ 371 Date: Oct. 31, 1994

§ 102(e) Date: Oct. 31, 1994

[87] PCT Pub. No.: WO93/19030

PCT Pub. Date: Sep. 30, 1993

[30] Foreign Application Priority Data

Mar. 17, 1992 [FI] Finland .................................. 921129

[51] Int. Cl.$^6$ .................................................. C07C 27/04
[52] U.S. Cl. ......................................... 568/864; 562/537
[58] Field of Search ............................ 568/864; 562/537

[56] References Cited

U.S. PATENT DOCUMENTS 5,096,820  3/1992  Leleu et al. ............................ 435/158

FOREIGN PATENT DOCUMENTS 0082277  6/1983  European Pat. Off. ..
0515498  8/1985  European Pat. Off. ..
0421882  4/1991  European Pat. Off. ..
0423525  4/1991  European Pat. Off. ..

OTHER PUBLICATIONS

Patent Abstracts of Japan, vol. 83, No. 7, 6, Apr. 1983.

*Primary Examiner*—Rebecca Cook
*Attorney, Agent, or Firm*—Bacon & Thomas

[57] ABSTRACT

A method for producing xylitol from D-glucose, D-fructose, D-galactose or mixtures thereof, characterized in that it comprises the steps of:

a. oxidation of the starting material to an intermediate that consists mainly of L-xylonic acid, D-arabinonic acid, D-lyxonic acid or a mixture of at least two of said acids, whereby said acids are free or in the form of their salts, lactones or O-formyl derivatives;

b. treatment of said intermediate with a hydrogenation catalyst and hydrogen gas in one or several steps to a product consisting mainly of xylitol or a mixture of xylitol, arabinitol and ribitol;

c. and, if necessary, separation of xylitol from said product and, if said product consist mainly of said mixture of pentitols, feeding of the fractions of arabinitol and ribitol back to the preceding reaction step b.

20 Claims, No Drawings

PRODUCTION OF XYLITOL

This application is a 371 of PCT/BE93/00013 filed Mar. 17, 1993.

The invention relates to a method of producing xylitol from D-glucose, D-fructose, D-galactose or mixtures thereof.

Amongst the pentitols only xylitol possesses a commercially important value. Today the large scale production of xylitol is based on hydrogenation of D-xylose as described in U.S. Pat. No. 4,008,285. D-xylose is being prepared through hydrolysis of hardwood, straw, corn cobs, oat hulls or other xylan-rich plant material. D-xylose may also be recovered as a side produce from the acidic spent liquors of the sulphite process or other processes that are being used for pulping of hardwoods or other xylan-rich material.

The production costs of xylitol are relatively high because the yield of D-xylose is typically low and complex processes are needed for its purification. In the hope of a more cost-effective production method it has been suggested in several occasions that D-glucose should or could be used as a raw material in the synthesis of xylitol.

In principle the synthesis of xylitol via D-xylose from D-glucose looks very straightforward; the two molecules (D-xylose and D-glycose) are identical except for an additional hydroxymethyl group at C-5 atom of D-glucose. Because of the apparent similarity of the molecules most effort has been put on developing methods of selectively cleaving the bond between C-5 and C-6 atoms of D-glucose. Kiss et al. (Helv. Chim. Acta 58 (1975) 311) converted D-glucose to 1,2-O-isopropylidene-alpha-D-glucofuranose, oxidatively cleaved the bond between the C-5 and C-6 atoms with periodate, removed the protecting isopropylidene group through hydrolysis and finally hydrogenated the resulting xylo-dialdose to xylitol. Later Malmelin (M.Sc. thesis, Helsinki University of Technology, Espoo 1978) evaluated the chemical costs in this method and found them too high for a large-scale production.

At the end of the 1960'ies Onishi ja Suzuki (Appl. Microbiol. 18 (1969) 1031) introduced a fermentation process for making xylitol from D-glucose through D-arabinitol and D-threo-2-pentulose (D-xylulose) as intermediates. The yield of xylitol was, however, low (14%). Later the individual reaction steps of this process were developed by Ohmomo et al. (J. Ferment. Technol. 61 (1983) 373, 63 (1985) 331). They also presented a modification in which D-xylulose was treated with D-xylulose isomerase and the resulting mixture of D-xylulose and D-xylose fermented to xylitol. In another modification D-xylose was separated from the isomerization product mixture and converted to xylitol through hydrogenation as disclosed in EP-A-0,403,392. D-xylulose was returned to the isomerization stage. In one case the mixture of D-xylose and D-xylulose was hydrogenated as such followed by separation of xylitol from the product mixture by chromatography as disclosed in EP-A-0,421,882).

The aim of the invention is to provide for a method of producing xylitol in a way that differs essentially from all the other known methods of producing xylitol from D-glucose, according to which method it is possible not only to use D-glucose but also to use mixtures of D-glucose and D-fructose or D-glucose and D-galactose as the raw material. These mixtures are available as hydrolysates of sucrose and lactose respectively.

This aim is reached by the fact that the method comprises the steps of:

a. oxidation of the starting material to an intermediate that consists mainly of L-xylonic acid, D-arabinonic acid, D-lyxonic acid or a mixture of an least two of said acids, whereby said acids are free or in the form of their salts, lactones or O-formyl derivatives;

b. treatment of said intermediate with a hydrogenation catalyst and hydrogen gas in one or several steps to a product consisting mainly of xylitol or a mixture of xylitol, arabinitol and ribitol;

c. and, if necessary, separation of xylitol from said product and, if said product consist mainly of said mixture of pentitols, feeding of the fractions of arabinitol and ribitol back to the preceding reaction step b.

In comparison with the traditional method of producing xylitol a great advantage of this invention is that the starting materials (D-glucose and the hydrolyzates of saccharose and lactose) are abundant, cheap and readily available. The production of the starting materials is not bound together with the production of xylitol. Another advantage of the invention is that the production of xylitol can partly be coupled together with the production of L-ascorbic acid which can result in lower production costs. In this respect the method of Onishi and Suzuki and its modifications are less attractive because none of the intermediates is involved in the synthesis of any other commercially important product.

In a particular embodiment of the method according to the invention, xylitol is separated by means of chromatography.

In another particular embodiment of the invention, the treatment with the hydrogenation catalyst and hydrogen gas is conducted at a pressure between 0.1 and 10 MPa and a temperature between 70° and 150° C.

As hydrogenation catalyst, use can be made of a ruthenium or nickel catalyst.

Other characteristics and advantages of the invention will become clear from the following description of a method for producing xylitol according to the invention. This description is given by way of example only and without being limitative in any way.

According to the invention D-glucose, D-fructose, D-galactose or mixtures thereof, particularly mixtures of D-glucose with D-fructose or D-galactose, are submitted to an oxidation in such way that L-xylonic acid, D-arabinonic acid, D-xylonic acid or a mixture of D-arabinonic and D-lyxonic acids is formed as an intermediate, said acids being free acids or in the form of their salts, lactones or O-formyl derivatives. The salts may for example include L-xylonate, D-arabinonate and D-xylonate. The lactones may include D-arabinonolactone and L-xylonolactone.

In a second step, said intermediate is treated with a hydrogenation catalyst and hydrogen gas in one or several steps in order to reduce the pentonic acids to the corresponding pentitols: xylitol, arabinitol and/or ribitol.

If the intermediate after oxidation is L-xylonic acid, mainly xylitol is formed and it is purified by chromatography.

In the other cases, when the intermediate after oxidation is D-arabinonic acid or D-lyxonic acid, the primary reduction product consists of D-arabinitol. This product is isomerized, and therefore the reaction is continued or another treatment with a hydrogenation catalyst and hydrogen gas is conducted so that a mixture of xylitol, arabinitol and ribitol is generated. Xylitol is then separated from this mixture, preferably by chromatography and the fractions of arabinitol and ribitol are returned to the preceding reaction stage.

The temperature during the hydrogenation is preferably between 70° and 150° C., more preferably between 100° and 130° C. At a temperature lower than 70° C. the reaction times are too long for a practical application while at temperatures higher than 150° C. the formation of side products is too extensive for an optimal production of pentitols. When there is an isomerization of D-arabinitol to xylitol, the overall yield of xylitol could be increased by using lower temperatures. However, the yield of xylitol obtained by conducting hydrogenation and isomerization in one step is lower than if hydrogenation and isomerization were conducted in two steps, which markedly increases the costs of the entire xylitol production process due to the increased costs associated with the isomerization and separation processes.

The pressure of hydrogen during the hydrogenation is preferably between 0.1 to 10 MPa, for example between 2–10 MPa for the isomerization of D-arabinitol.

As far as the pressure was in this range, the rate of the isomerization of D-arabinitol does not depend much on the pressure of hydrogen. Therefore the isomerization step is advantageously carried out at a lower temperature than the preceding hydrogenation step.

Suitable hydrogenation catalysts are ruthenium, especially ruthenium-on-carbon, or nickel, especially Raney-nickel.

Even trace amounts of formic acid can prevent the hydrogenation by the ruthenium-on-carbon catalyst. Small amounts of oxalic acid formed in the oxidation, do not prevent the hydrogenation. The ruthenium catalyst can be applied not only for the hydrogenation reaction but also for the isomerization of for instance D-arabinitol to xylitol.

Raney-nickel catalysts can be applied in the hydrogenation of the pentonic acids and their lactones, e.g. for the production of xylitol from D-arabinitol, provided that the dissolution of the catalyst can be prevented. A great advantage of the nickel catalyst is that formic acid may be present. It is therefore unnecessary to pay attention to a complete removal of the formic acid that is formed in the production of the pentonic acids. Most of the formic acids can be recovered by distillation of the de-ionized oxidation produce solution, while the residue can be hydrogenated without a further purification.

As to the intermediate to be subjected to the treatment with the hydrogenation catalyst and hydrogen gas, D-arabinonic acid may be prepared by oxidizing D-glucose with oxygen gas in an alkaline water-containing solution.

D-arabinonic acid is also formed as the main product in a similar oxidation of D-fructose (Carbohydr. Res. 141 (1985) 319). Therefore mixtures of D-glucose and D-fructose, such as hydrolyzates of saccharose, may also be used as the raw material in the process of producing xylitol according to the example.

When D-galactose is oxidized with oxygen in alkaline water-containing solutions, mainly a salt of D-lyxonic acid is formed. In the hydrogenation of D-lyxonic acid (or its lactone) mainly D-arabinitol (D-lyxitol) is formed. Therefore mixtures of D-glucose and D-galactose, such as hydrolyzates of lactose, may also be applied as the raw material in the process of producing xylitol according to the example.

Another way of producing D-arabinonic acid from D-glucose is to oxidize D-glucose with pyranose-2-oxidase to D-arabino-hexos-2-ulose (U.S. Pat. No. 4,423,149) and to treat this with hydrogen peroxide (Carbohydr. Res. 127 (1984) 319) or other hydroperoxides. Also in this case formic acid is formed as a side product. The reaction of D-arabino-hexos-2-ulose and hydrogen peroxide is fastest and most selective in alkaline solutions while the product comprise the salts of D-arabinonic and formic acids. Under acidic conditions e.g. performic acid (i.e. a mixture of formic acid and hydrogen peroxide) may be applied as the oxidant. 0.3M D-erythro-pentos-2-ulose can be oxidized with 0.6M performic acid. The reaction is complete in 10 minutes and results in the formation of D-erythrono-1,4-lactone, 3- and 4-o-formyl-D-erythronic acids and the unsubstituted D-erythronic acid. The o-formyl groups are rapidly hydrolyzed in an aqueous solution.

Still another way of producing D-arabinonic acid is to oxidize D-glucose to D-arabino-2-hexulosonic acid (or its salt) and decarboxylate it with hydrogen peroxide or its salt (JP 15,610 ('63), Carbohydr. Res. 36 (1974) 283–291). D-arabino-2-Hexulosonic acid can be produced through fermentation (U.S. Pat. Nos. 3,255,093 and 3,282,795), catalytic oxidation (EP-A-O-,151,498) or a two-step enzymatic oxidation (U.S. Pat. No. 4,423,149). The advantage of the route via D-arabino-2-hexulosonic acid is that formic acid is not generated which enables a more direct hydrogenation of the de-ionized oxidation product mixture with the ruthenium catalyst.

The intermediate L-xylonic acid can be prepared by oxidative decomposition of L-sorbose which is produced from D-glucose as an intermediate in the large-scale synthesis of L-ascorbic acid.

L-xylonic acid can also be prepared by first fermenting D-glucose to L-xylo-2-hexulosonic acid as described in Appl. Environ. Microbiol. 43 (1982) 1064 and then treating it with hydrogen peroxide as described in JP 15,610 ('63) and Carbohydr. Res 36 (1974) p. 283–291. In this case, carbon dioxide is being generated as side-product instead of formic acid, which enables the hydrogenation of the de-ionized reaction product mixture with ruthenium catalysts.

Because L-sorbose and L-xylo-2-hexulosonic acids are intermediates in the commercial synthesis of L-ascorbic acid, the production of xylitol can be coupled with the production of the L-ascorbic acid.

The invention will be further illustrated in more detail in the following examples.

EXAMPLE 1

The oxidation and lactonisation were carried out as follows. An autoclave was charged with an aqueous solution of sodium hydroxide (18 g), water (264 g), methanol (100 g) and sodium arabinonate (16 g). After the initial charge the autoclave was sealed, air was replaced with oxygen, and an oxygen pressure of 1.1 HPa was applied under efficient mixing. The mixture was thermostated at 45° C. The reaction was started by pumping an aqueous solution of D-glucose (82%, 85° C.) at a constant rate (5ml/min., 1050 g glucose solution). Simultaneously, an aqueous solution of sodium hydroxide (821 g NaOH, 47% d.s.) was pumped at a rate of circa 3 ml/min. The temperature of the reaction mixture was constantly monitored and kept at 45° C. After stopping the pumping of D-glucose solution, the pumping of aqueous sodium hydroxide was still continued until all NaOH solution was added.

At a conversion degree of 98% of glucose, oxygen pressure was released and the reaction mixture was removed from the autoclave at 45° C. The sodium arabinonate crystals formed were separated by centrifugation and washed with aqueous methanol. An amount of 741 g sodium arabinonate (3.9 mol) was obtained.

One mole of sodium arabinonate (188 g) in 300 ml of water was acidified on an acid cation exchange resin, giving a solution of arabinonic acid. The arabinonic acid was transformed into the γ-lactone by concentrating in vacuum the aqueous solution to about 200 ml when 300 ml of butanol is added. After a third concentration, the solution is removed from the flask with the aid of 100 ml of butanol and seeded. Crystallization begins at once and a large crop of crystals forms. The crystalline product (115 g) is collected on a filter, washed with butanol and dried.

To a pressure reactor were added 0.12 mol (18 g) D-arabinono-1,4-lactone, 0.5 g 5% ruthenium-on-carbon catalyst and 18 ml water. The pressure of hydrogen gas was adjusted to 8 MPa, an efficient mixer was turned on and the temperature was raised to 130° C. The reaction was interrupted after 8 h while the consumption of hydrogen gas was two-fold in comparison with the molar amount of the starting material. The yield of arabinitol was 90 mol-% of D-arabinono-1,4-lactone. The reaction solution was filtered and concentrated while D-arabinitol crystallized.

To the pressure reactor were added 20 mmol (3 g) D-arabinitol, 0.3 g 5% ruthenium-on-carbon catalyst and 20 ml water. The pressure of hydrogen gas was adjusted to 8 MPa, the mixer was turned on and the temperature was raised to 130° C. An equilibrium between arabinitol, xylitol and ribitol was attained within 10 h. After a shorter reaction time of 5 h the product composition was: 60% arabinitol, 20% xylitol, 13% ribitol and 7% other products. When the catalytic reaction was carried out at lower temperatures, less of the other products were formed in comparison with xylitol and ribitol whereas the equilibrium between the pentitols shifted towards arabinitol.

According to this example a mixture of xylitol, arabinitol and ribitol was prepared from D-glucose through D-arabinonic acid. Xylitol has been separated from this mixture by chromatography (Chem. Zvesti 34 (1980) 530) whereas the fractions of arabinitol and ribitol have been returned to the last catalytic treatment in order to make more xylitol.

This example shows that the hydrogenation of pentonic acids (or their lactones) can be carried out at very high concentrations, in this case in a 50% (w/w) solution and that ruthenium catalysts can be applied not only for the hydrogenation step, but also for the isomerization step.

The selectivity of the hydrogenation of D-arabinono-1,4-lactone strongly depended on the temperature. For example at 70° C., the yield of arabinitol was 96%. At lower temperatures, the reaction times were too long and at temperatures higher than 150° C., the formation of side-products was too extensive. Increasing the pressure of hydrogen within the range of 2 to 10 MPa did increase the rate of hydrogenation. The rate of isomerization did however not depend much on the pressure of hydrogen.

EXAMPLE 2

D-glucose was oxidized in the same manner as in example 1.

To a pressure reactor were added 20 mmol (3 g) D-arabinono-1,4-lactone, 3 g of a Raney-nickel catalyst and 20 ml water. The pressure of hydrogen gas was adjusted to 8 MPa, an efficient mixer was turned on and the temperature was raised to 130° C. The reaction was interrupted after 5 h. The yield of D-arabinitol was 37% and no other reaction products were present. When 1 mmol (0.06 g) of formic acid was initially added to the reactor, the yield of D-arabinitol under similar conditions was 48%. No other products were formed.

EXAMPLE 3

Example 2 was repeated but the initial charge of formic acid was increased to 20 mmol (0.9 g).

The consumption of hydrogen gas was initially very fast and obviously all formic acid was converted to methanol in 3–4 h while the yield of D-arabinitol was 14%. After a reaction time of 6 h the yield of D-arabinitol was already 31%.

In the examples 2 and 3, the reaction solutions had an intensive green color. A gas-liquid chromatographic analysis also indicated that at the end of the reaction, a significant portion of the residual D-arabinonic acid was present as a salt. These facts together proved that the nickel catalyst was partly converted to soluble nickel (II) salts during the hydrogenation.

EXAMPLE 4

D-glucose was oxidized to sodium D-arabinonate as in example 1.

To a pressure reactor were added 20 mmol (3 g) D-arabinono-1,4-lactone, 5 mmol (0.2 g), sodium hydroxide, 3 g of a Raney-nickel catalyst and 20 ml water. The pressure of hydrogen gas was adjusted to 8 MPa, an efficient mixer was turned on and the temperature was raised to 130° C. The reaction was interrupted after 6 h. The overall yield of pentitols was 66% (60% arabinitol, 5% ribitol and 1% xylitol). The other main components in the reaction mixture were the 1,4-lactones and sodium salts of D-arabinonic and D-ribonic acids. The reaction solution was almost colorless.

According to this example the dissolution of the nickel catalyst was prevented by lowering the acidity of the reaction solution with an addition of alkali. The hydrogenation proceeded smoothly and the yield of pentitols was close to the maximum value of 75% in this case. The salts of pentonic acids, of course, did not undergo hydrogenation. On the contrary, sodium D-arabinonate was partly isomerized to sodium D-ribonate, and the subsequent hydrogenation of D-ribono-1,4-lactone resulted in enhanced formation of ribitol. In spite of the isomerization of the starting material, the control of pH can be applied in the production of xylitol from D-arabinonic acid as both arabinitol and ribitol yield xylitol in the second isomerization step. On the contrary, the control of pH can not be applied when L-xylonic acid is to be converted to xylitol.

The acidity of the reaction solution can naturally be brought about in several ways and by using several compounds. The essential point here is, however, that by controlling pH less of the catalyst is lost and its life-time is increased.

EXAMPLE 5

D-glucose was oxidized to sodium D-arabinonate as in example 1.

To a pressure reactor were added 20 mmol (3 g) D-arabinono-1,4-lactone, 3 g of a Raney-nickel catalyst (3 g), 3 ml water and 17 ml methanol. The pressure of hydrogen gas was adjusted to 8 MPa, an efficient mixer was turned on and the temperature was raised to 130° C. The reaction was interrupted after 6 h. The conversion of the starting material was 72% and the yield of arabinitol 68%. The reaction solution was colorless. Pare of the unreacted starting material was present as methyl D-arabinonate whereas the proportion of the free D-arabinonic acid was much smaller than in water.

The rate of the hydrogenation reaction depended little on the pressure of hydrogen in the range 4–10 MPa. However, at 2 MPa the reaction was much slower.

According to this example the dissolution of the nickel catalyst could be prevented by using aqueous methanol as the solvent instead of water. This effect was partly caused by a decreased proportion of the free D-arabinonic acid in the reaction mixture and probably also by a less pronounced dissociation of the free D-arabinonic acid. A similar effect can naturally be brought about by using organic solvents other than methanol.

Under the conditions of the example D-arabinonic acid was not isomerized to D-ribonic acid. Therefore a similar hydrogenation with Raney-nickel in mixtures of organic solvents and water can be applied for production of xylitol from L-xylonic acid.

EXAMPLE 6

D-glucose was oxidized to sodium D-arabinonate as in example 1.

To a pressure reactor were added 20 mmol (3 g) D-arabinitol, 3 g of a Raney-nickel catalyst and 20 ml water. The pressure of hydrogen gas was adjusted to 8 MPa, a mixer was turned on and the temperature was raised to 110° C. After 24 h the produce composition was: 58% arabinitol, 23% xylitol, 14% ribitol and 6% other products. At longer reaction times the yields of xylitol and ribitol were slightly higher in comparison with a much higher yield of the other products. Also with increasing temperature the yields of the other products increased faster than the yields of xylitol and ribitol.

According to this example Raney-nickel catalysts can be applied for production of xylitol from D-arabinitol. Xylitol can be separated from the reaction product mixture by chromatography (Chem. Zvesti 34 (1980) 530). Under the conditions of the example a yield of 80% of xylitol from D-arabinitol is possible when all arabinitol and ribitol is returned to the reaction.

EXAMPLE 7

D-glucose has been transformed to L-sorbose. This tranformation did occur in the large scale synthesis of L-ascorbic acid, wherein L-sorbose was formed from D-glucose as an intermediate.

5 g Sodium hydroxide and 150 ml 80% (w/w) methanol were added to a Teflon-lined pressure reactor and the solution was thermostated at 25° C. An efficient mixer was turned on and the pressure of oxygen gas was adjusted at 1 MPa. Aqueous solutions of L-sorbose (200 g, 35% (w/w)) and sodium hydroxide (64 g, 50% (w/w)) were added at a constant rate during a period of 2.5 h. The reaction was continued for an additional 2 h. The yield of sodium L-xylonate was 69 mol-%. The other main products were the sodium salts of formic, glycolic, glyceric and threonic acids.

The reaction solution was de-ionized with a cation exchange resin and concentrated to a syrup. The syrup was dissolved in 0.04M hydrogen chloride in 1,4-dioxane and its azeotrope with water was distilled off in order to promote the lactonization of L-xylonic acid. The residue was concentrated to a syrup, dissolved in water and eluted through a column of an anion exchange resin in the acetate form in order to remove the free acids. The eluate was concentrated to a syrup, dissolved in 0.04M hydrogen chloride in 1,4-dioxane and its azeotrope with water was distilled off. The residue was concentrated to a syrup and dissolved in acetonitrile. The solution was concentrated while L-xylono-1,4-lactone crystallized.

To a pressure reactor were added 20 mmol (3 g) L-xylono-1,4-lactone, 0.3 g 5% ruthenium-on-carbon catalyst and 20 ml water. The pressure of hydrogen gas was adjusted to 8 MPa, an efficient mixer was turned on and the temperature was raised to 130° C. The reaction was monitored by following the consumption of hydrogen gas. A theoretical amount of hydrogen (40 mmol) was consumed in 2 h while the yield of xylitol was 90–91 mol-% as determined by gas-liquid chromatography. The side products comprised mainly of arabinitol and threitol. The amount of the unconverted starting material was 1% of the original.

As pure xylitol was obtained, any separation by chromatography or other processes was not necessary.

The step of formation of the crystaline L-xylono-1,4-lactone was performed in order to purify the oxidation product mixture from formic acid, as it had been shown that even trace amounts of formic acid prevented the hydrogenation of said lactone and thus of the de-ionized oxidation product mixture of L-sorbose. Small amounts of oxalic acid formed in the oxidation did, on the contrary, not prevent the hydrogenation. This step of crystallization is not required if the oxidation product mixture can be purified from formic acid in another way.

The invention is in no way limited to the embodiments described herebefore and within the scope of the following claims, many modifications of this embodiments are possible.

I claim:

1. A method for producing xylitol from a starting material selected from the group consisting of D-glucose, D-fructose, D-galactose or a mixture thereof, comprising the steps of:
   a. oxidizing the starting material to an intermediate that consists essentially of L-xylonic acid, D-arabinonic acid, D-lyxonic acid or a mixture of D-arabinonic acid and D-lyxonic acid whereby said acid or mixture is free or is treated sequentially to produce its salt, lactone or O-formyl derivative; and
   b. treating said intermediate with a hydrogenation catalyst and hydrogen gas in one or several steps to produce a product comprising xylitol.

2. A method for producing xylitol, arabinitol and ribitol from a starting material selected from the group consisting of D-glucose, D-fructose, D-galactose or a mixture thereof, comprising the steps of:
   a. oxidizing the starting material to an intermediate that consists essentially of L-xylonic acid, D-arabinonic acid, D-lyxonic acid or a mixture of D-arabinonic acid and D-lyxonic acid whereby said acid or mixture is free or is treated sequentially to produce its salt, lactone or O-formyl derivative; and
   b. treating said intermediate with a hydrogenation catalyst and hydrogen gas in one or several steps to produce a product comprising a mixture of xylitol, arabinitol and ribitol.

3. The method of claim 2 further comprising a step of separating xylitol from the product.

4. The method of claim 3, wherein the xylitol is separated by means of chromatography.

5. The method of claim 2 further comprising a step of feeding fractions of arabinitol and ribitol back to reaction step b.

6. The method according to claim 1, wherein the treatment with the hydrogenation catalyst and hydrogen gas is conducted at a pressure between 0.1 and 10 MPa and a temperature between 70° and 150° C.

7. The method according to claim 6, wherein the pressure is between 2 and 10 Mpa.

8. The method according to claim 6, wherein the temperature is between 100° and 130° C.

9. The method according to claim 1, wherein the hydrogenation catalyst is a ruthenium or nickel catalyst.

10. The method according to claim 9, wherein the hydrogenation catalyst is ruthenium on carbon.

11. The method according to claim 9, wherein the hydrogenation catalyst is a Raney-nickel catalyst.

12. The method according to claim 1, wherein, said starting material is D-glucose and said intermediate consists essentially of L-xylonate, L-xylonic acid or L-xylonolactone, the intermediate being produced by fermenting the starting material to L-xylo-2-hexulosonic acid or its salt and decarboxylating it with hydrogen peroxide or its salt.

13. The method according to claim 1, wherein said intermediate consists essentially of D-arabinonate or a mixture of D-arabinonate and D-lyxonate, the intermediate being produced by treating said starting material with oxygen gas in the absence or presence of an oxidation catalyst in an alkaline, water-containing solution.

14. The method according to claim 1, wherein said starting material is D-glucose and said intermediate consists essentially of D-arabinonate, D-arabinonolactone, D-arabinonic acid or an O-formyl derivative of D-arabinonic acid, the intermediate being produced by oxidizing the starting material with pyranose-2-oxidase to D-arabino-hexos-2-ulose and by treating it with hydrogen peroxide or its salts.

15. The method according to claim 1, wherein said starting material is D-glucose and said intermediate consists essentially of D-arabinonate, D-arabinonolactone or D-arabinonic acid, the intermediate being produced by oxidizing the starting material enzymatically, catalytically or through fermentation to D-arabino-2-hexulosonic acid or its salt and decarboxylating it with hydrogen peroxide or its salt.

16. The method according to claim 1, wherein said starting material is D-glucose which is transformed into L-sorbose and said intermediate consists essentially of L-xylonic acid, and xylitol is formed by the treatment with a hydrogenation catalyst and hydrogen gas.

17. The method according to claim 1, wherein the starting material is a mixture of D-glucose and D-fructose.

18. The method according to claim 17, wherein the starting material is obtained from a hydrolysate of saccharose.

19. The method according to claim 1, wherein the starting material is a mixture of D-glucose and D-galactose.

20. The method according to claim 19, wherein the starting material is obtained from a hydrolysate of lactose.

* * * * *